US011911504B2

(12) United States Patent
Toker

(10) Patent No.: US 11,911,504 B2
(45) Date of Patent: Feb. 27, 2024

(54) APPARATUS AND METHOD FOR PROTECTING NEURONS AND REDUCING INFLAMMATION AND SCARRING

(71) Applicant: GALEN THERAPEUTICS LLC, Boston, MA (US)

(72) Inventor: Tunc Toker, Boston, MA (US)

(73) Assignee: GALEN THERAPEUTICS LLC, Boston, MA (US)

(*) Notice: Subject to any disclaimer, the term of this patent is extended or adjusted under 35 U.S.C. 154(b) by 0 days.

(21) Appl. No.: 16/966,683

(22) PCT Filed: Feb. 4, 2019

(86) PCT No.: PCT/US2019/016494
§ 371 (c)(1),
(2) Date: Jul. 31, 2020

(87) PCT Pub. No.: WO2019/152917
PCT Pub. Date: Aug. 8, 2019

(65) Prior Publication Data
US 2021/0052491 A1 Feb. 25, 2021

Related U.S. Application Data

(60) Provisional application No. 62/717,303, filed on Aug. 10, 2018, provisional application No. 62/667,834, filed on May 7, 2018, provisional application No. 62/625,535, filed on Feb. 2, 2018.

(51) Int. Cl.
A61K 9/00 (2006.01)
A61K 31/15 (2006.01)
A61K 31/555 (2006.01)
A61K 31/28 (2006.01)
A61L 27/50 (2006.01)
A61L 27/54 (2006.01)
A61L 27/58 (2006.01)
A61L 31/14 (2006.01)
A61L 31/16 (2006.01)
A61K 31/502 (2006.01)

(52) U.S. Cl.
CPC .......... A61K 9/0085 (2013.01); A61K 9/0019 (2013.01); A61K 31/15 (2013.01); A61K 31/28 (2013.01); A61K 31/502 (2013.01); A61K 31/555 (2013.01); A61L 27/50 (2013.01)

(58) Field of Classification Search
CPC .... A61K 9/0085; A61K 9/0019; A61K 31/15; A61K 31/555; A61K 2400/06; A61K 31/28; A61K 31/502; A61L 27/54; A61L 27/58; A61L 31/148; A61L 31/16; A61L 27/50; A61L 2300/204; A61L 2300/216; A61L 2400/06
See application file for complete search history.

(56) References Cited

U.S. PATENT DOCUMENTS

| 5,156,839 | A | 10/1992 | Pennell et al. |
| 5,785,993 | A | 7/1998 | Baker et al. |
| 7,001,431 | B2 | 2/2006 | Bao et al. |
| 7,202,281 | B2 | 4/2007 | Cohn et al. |
| 8,394,399 | B2 | 3/2013 | Young et al. |
| 9,226,948 | B2 | 1/2016 | Lopes et al. |
| 9,289,279 | B2 | 3/2016 | Wilson et al. |
| 9,326,934 | B2 | 5/2016 | Gravett et al. |
| 9,561,311 | B2 | 2/2017 | Becker et al. |
| 9,585,983 | B1 | 3/2017 | Brahm |
| 9,598,383 | B2 | 3/2017 | Cohen et al. |
| 9,675,696 | B2 | 6/2017 | Chamness |
| 9,782,432 | B2 | 10/2017 | Uhrich et al. |
| 2002/0177558 | A1 | 11/2002 | Meyerhoff et al. |

(Continued)

FOREIGN PATENT DOCUMENTS

| AU | 2004208821 B2 | 1/2009 |
| CA | 2817215 C | 5/2012 |

(Continued)

OTHER PUBLICATIONS

Bernardy, Catia CF, et al. "Tempol, a superoxide dismutase mimetic agent, inhibits superoxide anion-induced inflammatory pain in mice." BioMed research international 2017 (2017). (Year: 2017).*
Orestes, Peihan, et al. "Free radical signalling underlies inhibition of CaV3. 2 T-type calcium channels by nitrous oxide in the pain pathway." The Journal of physiology 589.1 (2011): 135-148. (Year: 2011).*
Wang, Zhi-Qiang, et al. "A newly identified role for superoxide in inflammatory pain." Journal of Pharmacology and Experimental Therapeutics 309.3 (2004): 869-878. (Year: 2004).*
Vincent et al., Evaluation of the compounds commonly known as superoxide dismutase and catalase mimics in cellular models, Journal of Inorganic Biochemistry, vol. 219, pp. 1-10. (Year: 2021).*
Doctow, et al., "Salen MN Complexes are Superoxide Dismutase/Catalase Mimetics that Protect the Mitochondria," Current Inorganic Chemistry, vol. 2, Sep. 2012, pp. 325-334.

(Continued)

Primary Examiner — Abigail Vanhorn
(74) Attorney, Agent, or Firm — ArentFox Schiff LLP

(57) ABSTRACT

A device for protecting neurons and reducing inflammation and adhesion formation following surgery is provided. Also provided is a method for protecting neurons and reducing inflammation and adhesion formation following surgery. The device includes a bioabsorbable substrate and a layer of an oxidation inhibitor mimicking the effects of superoxide dismutase and catalase enzymes located on a surface of the substrate. Oxidation inhibitors that may be used include EUK-8, EUK-134, EUK-189, and EUK-207 (a mimetic of superoxide dismutase/catalase), monosodium luminol or phenyl N-t-butylnitrone or an analog with similar antioxidant properties. The oxidation inhibitors reduce oxidative stress and trigger the subject's natural anti-oxidant and anti-inflammatory defenses, thereby reducing neuron death, loss of neuron connectivity, inflammation and scarring and restoring excitatory function of neurons.

11 Claims, 11 Drawing Sheets

(56) References Cited

U.S. PATENT DOCUMENTS

| | | |
|---|---|---|
| 2003/0228346 A1 | 12/2003 | Herrmann |
| 2004/0059107 A1 | 3/2004 | Malfroy-Camine et al. |
| 2004/0076661 A1 | 4/2004 | Chu et al. |
| 2004/0229878 A1 | 11/2004 | DiMauro et al. |
| 2005/0173245 A1 | 8/2005 | Feldman et al. |
| 2008/0069857 A1 | 3/2008 | Yeo et al. |
| 2008/0187591 A1 | 8/2008 | Rhee et al. |
| 2009/0004243 A1 | 1/2009 | Pacetti et al. |
| 2009/0004276 A1 | 1/2009 | Ben-Shalom et al. |
| 2009/0131377 A1 | 5/2009 | Salvemini |
| 2010/0196481 A1 | 8/2010 | Pritchard et al. |
| 2010/0198331 A1 * | 8/2010 | Rapoza ............. A61F 2/91 623/1.15 |
| 2010/0291055 A1 | 11/2010 | Athanasiadis et al. |
| 2011/0176994 A1 | 7/2011 | Pratt et al. |
| 2012/0189619 A1 | 7/2012 | Binette |
| 2014/0155916 A1 | 6/2014 | Hodgkinson |
| 2015/0374798 A1 | 12/2015 | Labhasetwar et al. |
| 2019/0136018 A1 | 5/2019 | Marcolongo et al. |
| 2020/0297631 A1 | 9/2020 | Batrakova et al. |

FOREIGN PATENT DOCUMENTS

| | | | |
|---|---|---|---|
| JP | 2011508789 A | | 3/2011 |
| TW | I442925 B | | 7/2014 |
| WO | WO-2005000283 A2 * | 1/2005 | ......... A61B 17/7061 |
| WO | 2006031376 A2 | | 3/2006 |
| WO | 2007036952 A2 | | 4/2007 |
| WO | 2013049049 A1 | | 4/2013 |
| WO | 2014116717 A1 | | 7/2014 |

OTHER PUBLICATIONS

Reddy, et al. "Neuroprotective Effects on the Drug GVT (monosodium luminol) are Mediated by the Stabilization of Nrf2 in Astrocytes," Neurochemistry International, vol. 56, 2010, pp. 780-788.

Khansari, et al., "Chronic Inflammation and Oxidative Stress as a Major Cause of Age Related Diseases and Cancer," Recent Patents on Inflammation & Allergy Drug Discovery, vol. 3, 2009, pp. 73-80.

Melov, et al., "Extension of Life-Span with Superoxide Dismutase/ Catalase Mimetics," Science, vol. 289, 2000, pp. 1567-1569.

Rosalind A Rosenthal et al. "Orally available MN porphyrins with superoxide dismutase and catalase activities", JBIC Journal of Biological Inorganic Chemistry, Springer, Berlin, DE, vol. 14, No. 6, Jun. 6, 2009.

Extended European Search Report dated Oct. 4, 2021, in related European application No. 19746928.1.

* cited by examiner

APPARATUS AND METHOD FOR PROTECTING NEURONS AND REDUCING INFLAMMATION AND SCARRING

RELATED APPLICATIONS

This application is a National Stage Entry of PCT/US2019/016494, filed Feb. 4, 2019, which claims priority to U.S. Provisional Application No. 62/717,303, filed on Aug. 10, 2018, U.S. Provisional Application No. 62/667,834, filed on May 7, 2018, and U.S. Provisional Application No. 62/625,535, filed on Feb. 2, 2018, each of which is hereby incorporated by reference in its entirety.

BACKGROUND

Oxidative stress caused by free radicals is known to modulate physiological and pathological processes across a wide spectrum of disorders and biological processes including degenerative diseases (bone, spine, neurological), autoimmune diseases, carcinogenesis, inflammation, aging, and development. Oxidative stress also plays a key role in wound healing and response to injury and in anti-inflammatory responses mediated by neutrophils and macrophages. Further, oxidative stress causes damage to neurons and is associated with neuronal trauma and death, eventually resulting in pain, paralysis, and mobility restriction in a variety of disease states.

Areas where reactive oxygen species cause damage include surgical intervention and diseases of the spine such as degenerative disc disease, spondylolisthesis, spondylolysis, osteomyelitis, stenosis, disc herniation, and scoliosis. Degenerative disc disease and deformations in the spine lead to high levels of oxidative stress in the affected area. Oxidative stress is caused by the inflammation of the disc or the deformed area of the spine primarily through pro-inflammatory cytokines such as IL-1β, IL-6, and TNF-α (Zhang et al https://www.ncbi.nlm.nih.gov/pmc/articles/PMC2785020/). These pro-inflammatory cytokines contribute to pathological pain. The degenerating disc also releases radical species as the cells continue to die, further increasing oxidative stress, and causing a domino effect.

During surgical intervention, tissue is exposed to high level of free radicals from the environment causing oxidative stress across a multitude of complex layers of the tissue. This results in a cascade of events driven by inflammatory responses to the stress. Each layer of the tissue has a different natural defense mechanism to fight oxidative stress. The exact mechanisms of these defenses are not understood. However, it is known that a variety of radical scavenging pathways are activated upon detection of high levels of free radicals.

Many studies present clear evidence that oxidative stress contributes to pathologies of chronic neurodegenerative disease in addition to the effects of the pro-inflammatory cytokines and radical species caused by necrosis. Oxidative stress kills GABA neurons and suppresses the excitatory activity of the surviving GABA neurons. (Yowtak et al., *Pain.* 2011 April; 152(4):844-52; Gwak et al., *Neuropharmacology,* 2011 April; 60(5):799-808; and Meisner et al., *J Neurotrauma,* 2010 April; 27(4):729-37). Even if the neurons survive, the oxidative stress and suppression of the firing activity of the surviving neurons are experienced as pain by the brain. In certain spinal injury related procedures, such as laminotomy, laminectomy and discectomy, tissue damage during surgery and biological responses to surgery can also lead to oxidative stress that in turn promote inflammation and neurological damage, which can lead to paralysis. Studies also link neurological damage to pain experienced by patients. Reducing oxidative stress can lower excess inflammation and neuronal death, slow degeneration of the disc, and restore excitatory function of GABA neurons, thereby eliminating pain and increasing motor function.

In addition to neuronal damage, surgical interventions can lead to complications including tissue and muscle damage and formations of granulation tissue commonly called scarring during recovery. These complications can also result in morbidity, pain, and motility constriction as well as scar tissue that can press on the neuron.

After spine surgery many patients experience severe pain and millions in the US and around the world live with chronic pain. Also, millions of patients experience severe limb and neck pain and live with chronic pain due to diseases of the spine including degenerative disc disease, spondylolisthesis, spondylolysis, osteomyelitis, stenosis, disc herniation, and scoliosis. There has been extensive research into pain generators that cause chronic pain as well as chronic radicular pain (commonly known as failed back surgery syndrome). Key pain generators include neuron trauma and death, loss of neuron connectivity, muscle trauma and spasms, excess inflammation, abnormal spinal nerve growth, scarring around neurons, and further degeneration of the spine. Studies indicate that a combination of these effects is what causes severe pain and it is difficult to associate pain with one single pain generator.

Various approaches for preventing neuronal damage during and after surgery and preventing excess inflammation and scarring have been explored till date. Physical therapy and exercise is a common starting point for patients with back pain. Steroid injection into the epidural as well as the disc space is also a commonly applied technique to reduce inflammation and eliminate pain. There has been extensive research in using physical barriers to prevent tissue binding and scarring in the critical phases of recovery in the operative setting. Anti-inflammatory and anti-allergen drugs have been investigated, both as stand-alone drugs and as drugs administered together with delivery vehicles that act as physical barriers. Collagen inhibitors and proteolytic enzymes also have been investigated for preventing adhesion formation. Anti-oxidant regimens have also been researched. However, all of these approaches have fallen short of alleviating chronic pain. The effects of steroid injections are short lived and there is controversy in the medical field with respect to the presumed efficacy of this technique. The bioavailability of anti-oxidant agents that have been tested have proved to be unsatisfactory. Human clinical trials have demonstrated that adhesion barriers alone do not alleviate pain even if they can prevent scarring. Anti-inflammatory drugs alone have not been able to address the complex state of pain and mobility restriction either. There is a need for a comprehensive solution that addresses the complications caused by oxidative stress including neuron damage, inflammation and scarring simultaneously, as these complications, in concert, cause pain and mobility.

Approaches that have been tried for preventing neuronal damage include the use of anti-oxidant agent superoxide dismutase and catalase enzymes delivered on nanoparticles to protect spinal neurons via reduction of oxidative stress. However, enzymes, while shown to be effective, are proteins and as such, are difficult to manufacture, not as stable as low molecular weight synthetic molecules, and present hurdles related to bioavailability and metabolism.

There exists a need for developing improved methods that simultaneously prevent neuronal damage and reduce inflammation and scarring post-surgery and for patients with chronic back pain while also addressing bioavailability and manufacturing complexities.

SUMMARY

The present technology is directed to devices and methods for prevention of neuron damage and reduction of inflammation and scarring between tissue surfaces or cavities such as spinal canal, disc space, and joint surfaces and promote tissue recovery. The technology includes administering an oxidation inhibitor or an analog thereof in a prolonged manner to protect neurons and inhibit formation of adhesions, reduce inflammation, and reduce pain. The oxidation inhibitor cycles radical oxygen species and transforms them into harmless agents by essentially sacrificing itself throughout the reaction process and supports body's inherent defenses to scavenge radical oxygen species. The oxygen inhibitor is delivered in a manner that ensures prolonged effect and addresses the historically challenging bioavailability issue of molecules.

Such inhibitors include, but are not limited to EUK-207, a small molecule mimetic of the enzymes superoxide dismutase and catalase, monosodium luminol, and phenyl N-t-butylnitrone. These inhibitors share a similar mechanism of action. Other agents such as glycyl-L-histidyl-L-lysine (prezatide) that can reduce oxidative stress and mimic the effects of superoxide dismutase and catalase enzymes may also be used in the methods and devices described herein. The oxidation inhibitor is administered in a localized manner with the help of a delivery vehicle that makes it possible for the inhibitor to persist for prolonged periods, e.g., several weeks. Specifically, it is administered on a substrate. This method of administering an oxidation inhibitor can be used to protect neurons, reduce inflammation, and prevent adhesion formation in the spinal canal or the disc space in lieu of epidural steroid injections following laminectomy, discectomy, fusions, or other types of interventions. This method applies to pan spine applications including complications with cervical, thoracic, lumbar, sacral and coccygeal structures. The technology is useful in other contexts as well, such as hip, knee, or joint replacement surgeries; severe trauma surgeries; gastro-intestinal interventions; and reconstructive surgery; where neuropathy, tissue healing and inflammation and formation of adhesions are significant concerns.

In accordance with one embodiment of the technology, a device for reducing scarring, accelerating recovery, and protecting neurons when applicable, includes a substrate and a first layer of an oxidation inhibitor. The oxidation inhibitor may, for example, be EUK-207 or highly purified monosodium luminol or phenyl N-t-butylnitrone. The substrate has a top surface and a bottom surface and may be bioabsorbable such that it is absorbed when inserted into an incision site within a subject and when in contact with the subject's tissue. The first layer of the oxidative inhibitor may be located on the top surface or the bottom surface of the substrate. The oxidation inhibitor triggers the subject's natural anti-oxidant and anti-inflammatory defenses, cycles reactive species and thus reduces neuronal death, inflammation and scarring. The oxidation inhibitor acts as a free radical scavenger and recycles itself allowing it to continue to act on cells restoring the electrical function, reducing inflammation. It regulates one or more key neurological proteins such as VEGF, Nrf2, and Bcl2, and acts on both pro- and anti-inflammatory cytokines. It also protects from mitochondrial induced cell death and prevents the action of neuronal damage.

The substrate can also be provided in a liquid or gel form. Accordingly, in one aspect of the technology, a method for treating pain associated with a disease of the spine in a subject in need thereof, is provided. The method requires injecting a pharmaceutical composition into a spinal space of the subject. The pharmaceutical composition comprises a bioabsorbable substrate and an oxidation inhibitor. The substrate is capable of being absorbed when injected into the spinal space and the oxidation inhibitor is capable of triggering the subject's anti-oxidant defenses, whereby the pain is reduced or eliminated. The substrate can be a gel or a foam. The gel can be in a nanoparticulate form and, in this case, the oxidation inhibitor can be encapsulated within the nanoparticles of the gel. The spinal space can be one or more spaces selected from the group consisting of: epidural space, disc space, subarachnoid space, nucleus pulposus, and intervertebral space. The disease the pain is associated with can be degenerative disc disease, spondylolisthesis, spondylolysis, osteomyelitis, stenosis, disc herniation, and scoliosis.

In some embodiments, the substrate may be customizable by a physician prior to insertion into the site of the disease. The substrate can be used as part of a minimally invasive spine surgery, open surgery or as a replacement to steroid injections as part of standard pain therapy. Additionally, the first layer of the oxidative inhibitor may be located on the bottom surface of the substrate, and may contact the subject's tissue upon insertion of the device into the site of disease of disease or complication. Alternatively, the first layer of the oxidation inhibitor may be located on the top surface of the substrate, while the bottom surface of the substrate may contact the subject's tissue upon insertion of the device into the site of disease of disease which can be the epidural, the disc space or a different location determined by the physician. In other embodiments, the device may include a second layer of the oxidation inhibitor. In such embodiments, the first layer of the oxidation inhibitor may be located on the top surface of the substrate, and the second layer of the oxidation inhibitor may be located on the bottom surface of the substrate. The second layer may contact the subject's tissue upon insertion of the device into the site of the disease (e.g., a spinal surgery incision). The substrate may be inserted into and enclosed within the site of the disease upon suturing of the site. The substrate may be a surgical film, sponge, scaffold, mesh, suture and/or a bioabsorbable polymer, and/or bioabsorbable implants such as cages, screws, brackets and/or biomaterials used in spine surgeries such as bone grafts.

In accordance with further embodiments, a method for protecting neurons, reducing inflammation and scarring is provided. The method includes providing a neuroprotective device. The device has (1) a substrate having a top surface and a bottom surface, and (2) a first layer of an oxidation inhibitor located on the top surface or the bottom surface of the substrate. The method may also include injecting the patient with a syringe or catheter (when the substrate is in the form of a gel or foam) or inserting the neuroprotective device into an incision site during an operation such that the substrate covers at least a portion of the tissue exposed by the incision, and closing the incision site (e.g., suturing the site closed with sutures) to secure the neuroprotective device within the site of disease. The substrate may be bioabsorbable such that it is absorbed when enclosed within the site of disease and in contact with the subject's tissue. The layer of oxidation inhibitor can reduce oxidative stress, trigger the subject's natural anti-oxidant and anti-inflammatory defenses, thereby reducing neuron death, excess inflammation and scarring.

In some embodiments, the sutures may be coated with an oxidation inhibitor. Additionally, or alternatively, the sutures may be infused with an oxidation inhibitor to similarly promote tissue health. Prior to closing the incision, the method may also include cutting the substrate to a physician determined size based upon the shape and size of the incision. Inserting the drug infused device into the site of disease may include inserting the neuroprotective device such that the first layer of oxidation inhibitor contacts the subject's tissue. The exact placement of the device will depend on surgeon's judgement and may differ from one case to another. The device can be planted in the epidural cavity post spine surgeries.

The device may also include a second layer of the oxidation inhibitor. The first layer of the oxidation inhibitor may be located on the top surface of the substrate, and the second layer of the oxidation inhibitor may be located on the bottom surface of the substrate. The incision site may be a spinal surgery incision.

In accordance with additional embodiments, a device for protecting neurons, reducing inflammation, and scarring includes a vehicle having at least one surface. The vehicle may be bioabsorbable such that it is absorbed when in contact with the subject's tissue. The device may also include a first layer of an oxidation inhibitor located on the at least one surface of the vehicle. The first layer of the oxidation inhibitor may trigger the subject's anti-oxidant defenses.

The vehicle may be a suture, a mesh, a scaffold, or a film.

The technology is further summarized by the following list of embodiments.

1. A device for protecting neurons, reducing inflammation and scarring, and accelerating tissue recovery, the device comprising: a substrate having a top surface and a bottom surface, the substrate capable of being absorbed when inserted into a site of disease within a subject where it is in contact with the subject's tissue; and a first layer of an oxidation inhibitor located on the top surface or the bottom surface of the substrate, wherein the layer is configured to trigger the subject's natural anti-oxidant defenses and cycle reactive species.
2. The device of embodiment 1, wherein the oxidation inhibitor is selected from the group consisting of EUK-8, EUK-134, EUK-189, and EUK-207.
3. The device of embodiment 2, wherein the oxidation inhibitor is EUK-207.
4. The device of embodiment 1, wherein the oxidation inhibitor is monosodium luminol or phenyl N-t-butylnitrone.
5. The device of embodiment 1, wherein the substrate is configured to be customizable by a physician prior to insertion into the site of disease.
6. The device of embodiment 1, wherein the first layer is located on the bottom surface of the substrate, the layer being configured to contact the subject's tissue upon insertion of the device into the site of disease.
7. The device of embodiment 1, wherein the first layer is located on the top surface of the substrate, the bottom surface of the substrate configured to contact the subject's tissue upon insertion of the device into the site of disease.
8. The device of embodiment 3, further comprising a second layer of EUK-207, the first layer being located on the top surface of the substrate, and the second layer being located on the bottom surface of the substrate and configured to contact the subject's tissue upon insertion of the device into the incision site.
9. The device of embodiment 4, further comprising a second layer of monosodium luminol or phenyl N-t-butylnitrone, the first layer being located on the top surface of the substrate, and the second layer being located on the bottom surface of the substrate and configured to contact the subject's tissue upon insertion of the device into the site of disease.
10. The device of embodiment 1, wherein the site of disease is degenerated or herniated disc, epidural cavity, weakened or structurally compromised lamina, space on top of dura matter or nucleus pulposus or a spinal surgery incision.
11. The device according to embodiment 1, wherein the substrate is configured to be inserted into and enclosed within the site of disease upon suturing of an incision site.
12. The device according to embodiment 1, wherein the substrate is a surgical film.
13. The device according to embodiment 1, wherein the substrate is a bioabsorbable polymer or a gel or a foam.
14. A method for protecting neurons and reducing inflammation and scarring in a subject, the method comprising, providing a device, the device comprising a substrate having a top surface and a bottom surface, wherein a first layer of an oxidation inhibitor is located on the top surface or the bottom surface of the substrate; inserting the device into a site of disease such that the substrate covers at least a portion of the tissue at the site of the disease; and closing an incision site at the site of the disease if the substrate is applied as part of a surgery, thereby securing the device within the site of disease; wherein the substrate is capable of being absorbed when inserted into the site of the disease within the subject where it is in contact with the subject's tissue, and the layer of oxidation inhibitor is configured to trigger the subject's anti-oxidant defenses, thereby protecting neurons and reducing inflammation and scarring.
15. The method of embodiment 14, wherein the oxidation inhibitor is selected from the group consisting of EUK-8, EUK-134, EUK-189, and EUK-207.
16. The method of embodiment 15, wherein the oxidation inhibitor agent is EUK-207.
17. The method of embodiment 14, wherein the oxidation inhibitor agent is monosodium luminol or phenyl N-t-butylnitrone.
18. The method of embodiment 14, wherein closing the incision site comprises suturing the incision site if the substrate is used during a surgery.
19. The method of embodiment 18, wherein the sutures are coated with one of EUK-8, EUK-134, EUK-189, EUK-207, monosodium luminol, and phenyl N-t-butylnitrone to further prevent neuron death and reduce scarring and inflammation.
20. The method of embodiment 19, wherein the sutures are infused with EUK-207 or monosodium luminol or phenyl N-t-butylnitrone to further prevent neuron death, scarring and reduce inflammation.
21. The method of embodiment 14, further comprising cutting the substrate to a physician determined size based upon a shape and size of the incision made during the surgery.
22. The method of embodiment 16, wherein the device is inserted such that the first layer of EUK-207 contacts the subject's tissue.
23. The method of embodiment 17, wherein the device is inserted such that the first layer of monosodium luminol or phenyl N-t-butylnitrone contacts the subject's tissue.

24. The method of embodiment 16, wherein the device further includes a second layer of EUK-207, the first layer being located on the top surface of the substrate, and the second layer being located on the bottom surface of the substrate.

25. The method of embodiment 17, wherein the device further includes a second layer of monosodium luminol or phenyl N-t-butylnitrone, the first layer being located on the top surface of the substrate, and the second layer being located on the bottom surface of the substrate.

26. The method according to embodiment 14, wherein the site of disease is degenerated or herniated disc, weakened or structurally compromised lamina, space on top of dura matter or nucleus pulposus or a spinal surgery incision site.

27. A device for reducing inflammation and scarring comprising, a vehicle having at least one substrate, the substrate capable of being absorbed when in contact with the subject's tissue; and a first layer of an oxidation inhibitor located on the at least one substrate of the vehicle, the first layer being configured to trigger the subject's anti-oxidant defenses, thereby reducing inflammation and scarring.

28. The device of embodiment 27, wherein the oxidation inhibitor is selected from the group consisting of EUK-8, EUK-134, EUK-189, and EUK-207.

29. The device of embodiment 27, wherein the oxidation inhibitor agent is EUK-207.

30. The device of embodiment 27, wherein the oxidation inhibitor agent is monosodium luminol or phenyl N-t-butylnitrone.

31. The device of embodiment 27, wherein the vehicle is at least one selected from the group consisting of a film, a suture, a mesh, and a scaffold.

32. A method for treating pain associated with a disease of the spine in a subject in need thereof, the method comprising, injecting a pharmaceutical composition into a spinal space of the subject, the pharmaceutical composition comprising a bioabsorbable substrate and an oxidation inhibitor, wherein the substrate is capable of being absorbed when injected into the spinal space and the oxidation inhibitor is capable of triggering the subject's anti-oxidant defenses, whereby the pain is reduced or eliminated.

33. The method of embodiment 32, wherein the spinal space is one or more spaces selected from the group consisting of: epidural space, disc space, subarachnoid space, nucleus pulposus, and intervertebral space.

34. The method of embodiment 32, wherein the oxidation inhibitor is selected from the group consisting of EUK-8, EUK-134, EUK-189, and EUK-207.

35. The method of embodiment 34, wherein the oxidation inhibitor is EUK-207.

36. The method of embodiment 32, wherein the oxidation inhibitor is monosodium luminol or phenyl N-t-butylnitrone.

37. The method of any of the embodiments 32-36, wherein the bioabsorbable substrate is a gel or a foam.

38. The method of embodiment 37, wherein the gel is a hydrogel.

39. The method of embodiment 32, wherein the reduction or the elimination of the pain is accompanied with reduction of elimination of inflammation associated with the disease.

40. The method of embodiment 32, wherein the reduction or the elimination of the pain is accompanied with reduction or elimination of neuronal injury associated with the disease.

41. The method of embodiment 32, wherein the disc space is nucleus pulposus.

42. The method of embodiment 32, wherein the disease is selected from the group consisting of degenerative disc disease, spondylolisthesis, spondylolysis, osteomyelitis, stenosis, disc herniation, and scoliosis.

BRIEF DESCRIPTION OF THE DRAWINGS

The foregoing features of embodiments will be more readily understood by reference to the following detailed description, taken with reference to the accompanying drawings, in which:

FIG. 4B is modified from a Figure in the article "Lumbar Spinal Stenosis," Orthopod®, https://eorthopod.com/lumbar-spinal-stenosis/, last accessed Feb. 2, 2018. FIG. 4C is modified from a Figure in the article "Explore Spinal Canal, The Nerve, and more!," Pinterest, https://www.pinterest.com/pin/561964859731841791/, last accessed Feb. 2, 2018.

DETAILED DESCRIPTION

Figure 1A:
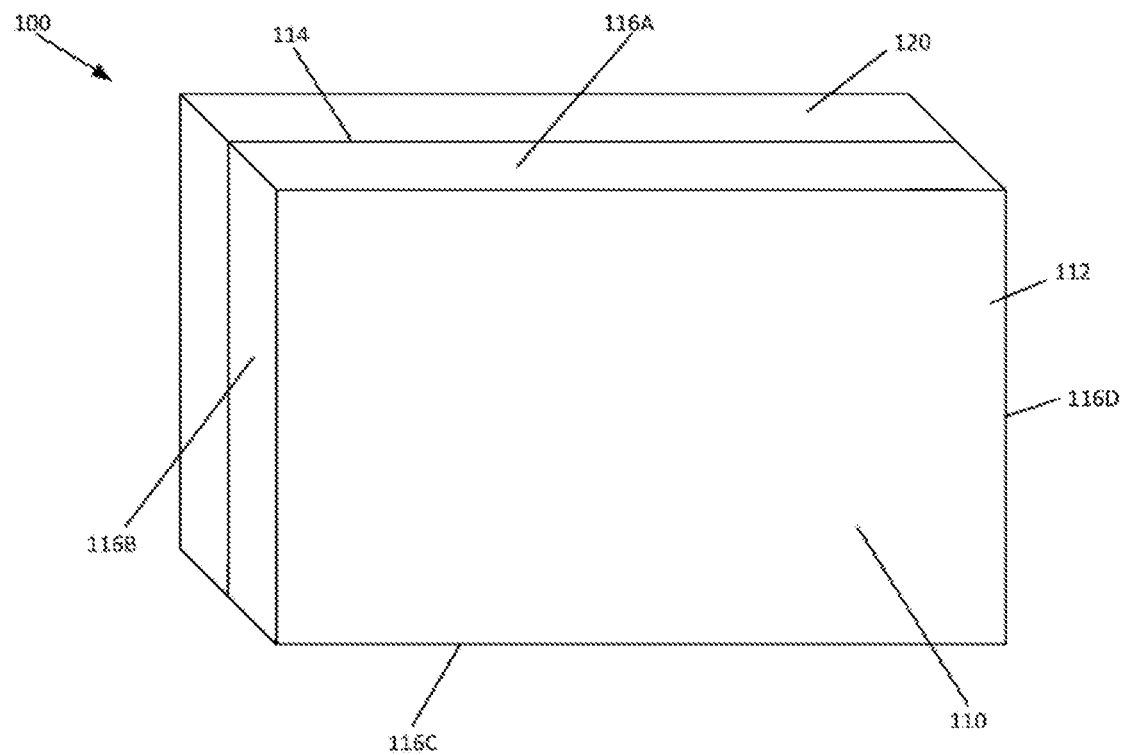
FIGS. 1A-1B schematically show one embodiment of a coated film, in accordance with various embodiments of the present technology.
Figure 1B:
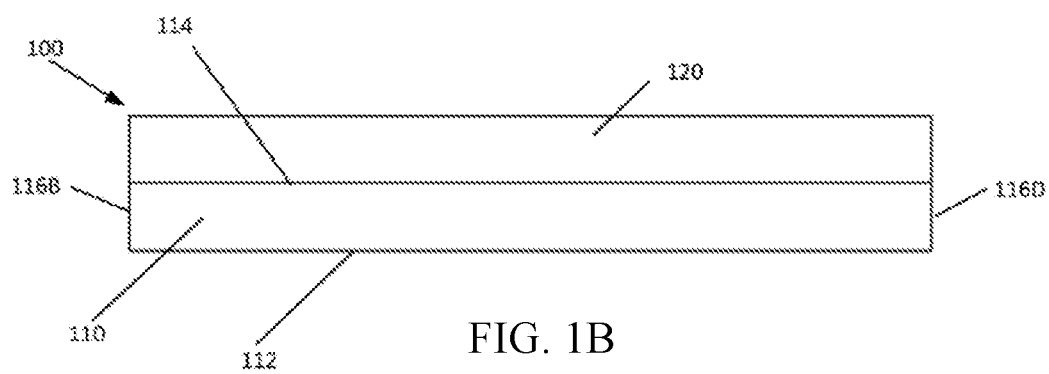

FIGS. 1A and 1B schematically show one illustrative embodiment of a coated vehicle 100 (e.g., a film) for protecting neurons and reducing inflammation and scarring within a patient. As shown in the Figures, the coated vehicle 100 includes a substrate 110 having a first surface 112 (e.g., a bottom surface), a second surface 114 (e.g., a top surface), and a number of side surfaces or edges 116A-D. In some embodiments, the substrate 110 may be bioabsorbable such that the substrate 110 is absorbed when inserted into a patient and in contact with the patient's tissue. For example, the substrate 110 may be an adhesion barrier that may be placed at the site of disease (discussed in greater detail below) to separate the internal tissue of the patient or on the epidural surface in the spine to protect neurons and prevent scarring and inflammation in the spinal canal. The exact application would vary from procedure to procedure.

The substrate 110 may be made from any number of material including bioabsorbable polymers. In particular, the substrate may be polycaprolactone, polylactic acid, polyglycolic acid, polyethylene glycol, polyethylene glycol, polyvinyl alcohol, glycerine, salts or a water soluble crystalline solid, silica, hydroxyapatite, calcium phosphate, or bioglass (or a combination thereof) to name but a few examples. Delivery systems based on biodegradable polymers or gels include syringes, catheters, pumps, fibers, films, foams, or filaments, comprising the active agents, or analogs thereof. Substrate 110 can also be hydrogel or fibrin based, including PHEMA/PHPMA, HAMC or agarose hydrogels, solidified gels, natural hydrogens such as protein hydrogel fibrins, or synthetic hydrogels such as PEG or electrospun fibers including collagen fibers. Such films, gels, collagens, sutures, fibers, foams, and filaments and particles can be prepared by a variety of processes known to those skilled in the art. Examples of substrates that may be used in the devices described herein are SYNVISC (Biomatrix, Inc., Ridgefield, N.J), Interceed (Johnson and Johnson), TephaFLEX (Tepha Medical Devices), SEPRAFILM (Genzyme Corporation), and SprayGel by Covidien. It should be noted that, although FIGS. 1A and 1B show substrate 110 as being rectangular, the substrate may have any shape and its size may vary. For example, substrate 110 may be round, square, triangular, or elliptical. As discussed in greater detail below, substrate 110 may also be physically customizable at the time of insertion into the patient (e.g., it may be cut or otherwise modified by the physician to suit the needs of the individual patient and/or procedure). The substrate may also have the form of a gel.

As noted above, the coated vehicle 100 may be used to promote neuron health, slow degeneration (e.g., disc degeneration) or reduce scarring and inflammation at the site of disease. To that end, one or more of the surfaces of substrate 110 may be coated with a drug/molecule. For example, the top surface of the substrate 110 may be coated with a layer of EUK-207 or monosodium luminol or phenyl N-t-butylnitrone, compounds known to exhibit anti-oxidant, anti-inflammatory, and neuro-protective effects.

EUK-207 is a member of a class of synthetic low molecular weight compounds known as salen Mn complexes. Other members of this class of compounds include EUK-8, EUK-134 and EUK-189. A brief overview of the biological effects of Salen Mn complexes can be found in Doctrow S R et al., *Current Inorganic Chemistry*, 2012, 2, 325-334 and references cited therein. Salen Mn complexes mimic the antioxidant enzymes superoxide dismutase (SOD) and catalase and scavenge superoxide and hydrogen peroxide, respectively. Salen Mn complexes have been shown to also scavenge reactive nitrogen species (RNS). Their low molecular weight, catalytic scavenging mechanism, and activity against multiple damaging species make them preferred antioxidants compared to other antioxidants such as non-catalytic ROS scavengers or proteinaceous antioxidant enzymes. Compared with proteinaceous antioxidant enzymes, these low-molecular-weight synthetic complexes are expected to have better stability and bioavailability. Also, their catalytic mode of action makes them more potent than traditional low molecular-weight antioxidant compounds.

Salen Mn complexes EUK-8, EUK-134, and EUK-189 have for long been known to exhibit cytoprotective effects in different systems. EUK-207 (see structure below) is a "second generation" cyclized salen Mn complex.

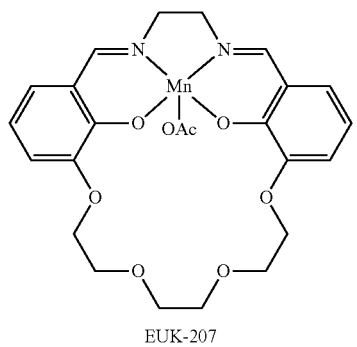

EUK-207

Its catalytic properties are equivalent to those of EUK-134 and EUK-189, but it has greater stability. Salen Mn complexes have been demonstrated to exhibit beneficial effects in many in vivo models of disease/injury. In some of these models, in addition to being protective, they have been found to suppress biochemical indicators of oxidative stress, such as oxidative modifications of protein, lipids and nucleic acids. Furthermore, lipid peroxidation in isolated cardiac mitochondria has been found to be reduced in hearts treated with EUK-207. Reactive oxygen species are also known to be produced by inflammatory cells. The salen Mn complex, EUK-207, has been shown to reduce excessive inflammatory and cell death responses associated with immunopathogenic response to influenza virus infection. Reactive oxygen species are produced by mitochondria too. At the same time, mitochondria are also a target of oxidative injury. In this regard, salen Mn complexes have been shown to also possess "mito-protective" activity, i.e., an ability to attenuate mitochondrial injury, in several experimental systems.

EUK-207 is also believed to acts as a stabilizer and regulator of the Nrf2 pathway (Clausen et al https://www.ncbi.nlm.nih.gov/pubmed/22406441) which is involved in the upregulation of cellular antioxidant defenses of the human body. The Nrf2 pathway has been demonstrated, for example, to be critically involved in the regulation of the basal expression and chemical induction of several antioxidants and phase 2 enzymes in cardiac fibroblasts, and an important factor in controlling cardiac cellular susceptibility to reactive oxygen and nitrogen species-induced cytotoxicity (Zhu et al., *FEBS Lett.* 2005 Jun. 6; 579(14):3029-36). Specifically, the Nrf2 pathway was shown to be required for the 3H-1,2-dithiole-3-thione (D3T) mediated induction in cardiac fibroblasts of superoxide dismutase, catalase, reduced glutathione, glutathione reductase, glutathione peroxidase, GSH S-transferase, and NAD(P)H:quinone oxidoreductase-1. Thus, EUK-207 is expected boost and prolong the anti-oxidant defenses (e.g., the natural anti-oxidant defenses) of the body through scavenging free radicals.

Monosodium luminol or phenyl N-t-butylnitrone too are thought to stabilize and regulate the Nrf2 pathway and as such, can boost the body's anti-oxidant defenses.

Further, in a study testing the effects of EUK134, another synthetic superoxide dismutase/catalase mimetic, several indices of oxidative stress and neuropathology produced in the rat limbic system by seizure activity elicited through systemic kainic acid (KA) administration were found to be reduced (Rong et al., *Proc. Natl. Acad. Sci. USA* Vol. 96, pp. 9897-9902, August 1999). Specifically, pretreatment of rats with EUK-134 was found to produce a reduction in increased protein nitration, activator protein-1- and NF-kBbinding activity, and spectrin proteolysis, as well as in neuronal damage resulting from seizure activity in limbic structures. It had been previously shown that DNA-binding activity of activator protein-1 and NF-kB, generally considered to be markers of cellular insults, was increased in these structures after KA induced seizure activity in adult rats (Rong, Y. & Baudry, M. (1996) *J. Neurochem.* 67, 662-668).

In light of the oxidative exposure of the skin and tissue during surgical intervention and the fact that oxidation inhibitors such as EUK-207, monosodium luminol, or phenyl N-t-butylnitrone trigger natural anti-oxidant and anti-inflammatory defenses of the human body, these oxidation inhibitors are believed to accelerate recovery and prevent formation of excessive fibroblasts and protect from neuronal damage. Additionally, with the use of a polymer-based delivery vehicle such as a film, gel, mesh, or scaffold, the concentration and effectiveness of the oxidation inhibitors is expected to remain sufficiently high throughout the most critical days post operation. In this manner, the coated vehicle is expected to significantly prevent neuron death, restore excitatory function of neurons, and reduce scar tissue and inflammation, compared to recovery without the aid of oxidation inhibitors.

Salen Mn complexes have certain advantageous features. For example, these complexes are low molecular weight synthetic compounds and as such, can be expected to have better stability and bioavailability in addition to being easier to manufacture, and like proteinaceous antioxidant molecules such as superoxide dismutase and catalase, they have a catalytic mode of action. Also, these complexes (based on results obtained from EUK-207 studies), can upregulate the basal expression and chemical induction of a number of antioxidants and phase 2 enzymes, which points to the preferability of using these complexes over enzymes for inhibiting oxidative stress.

Figure 2:
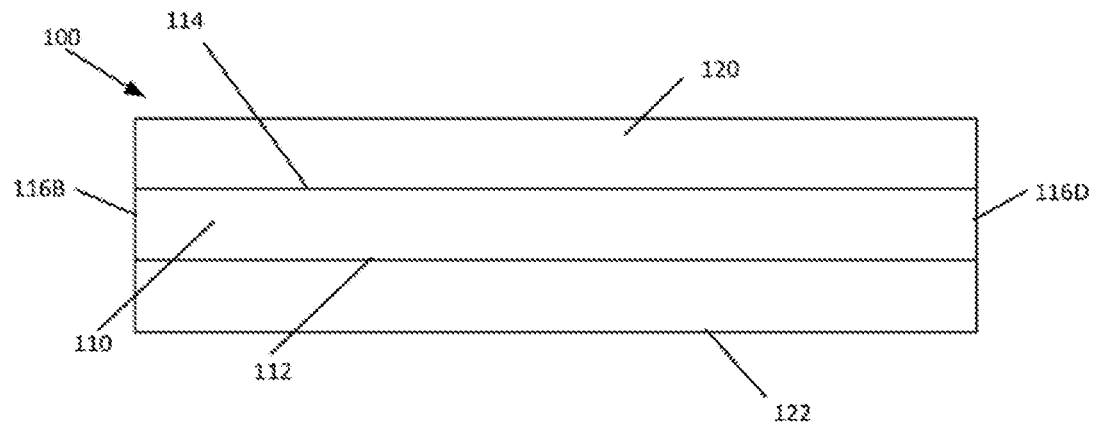
FIG. 2 schematically shows an alternative coated film, in accordance with additional embodiments of the present technology.
Figure 3:
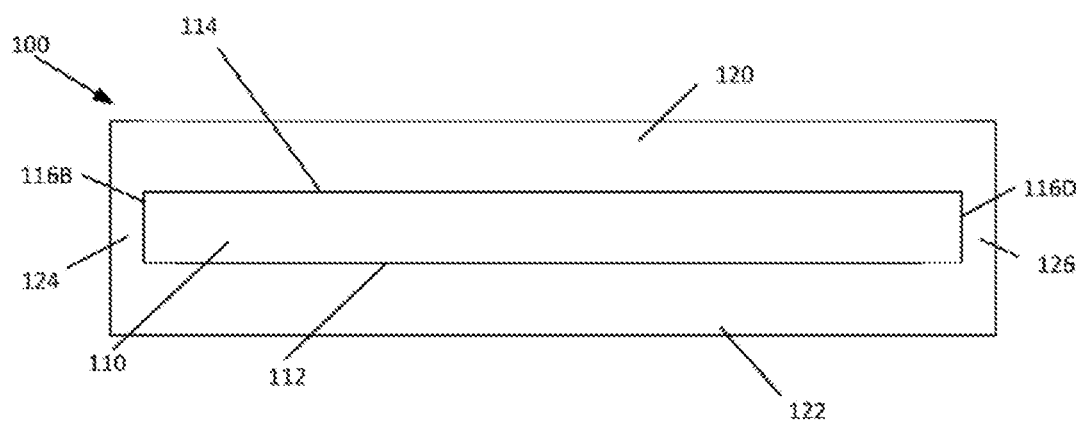
FIG. 3 schematically shows an additional alternative embodiment of a coated film in accordance with further embodiments of the present technology.

Although the layer of oxidation inhibitor is discussed above as being applied to the top surface 114 of the substrate 110, in some embodiments, the layer of oxidation inhibitor may be applied to the bottom surface 112 of the substrate. Additionally, or alternatively, as shown in FIG. 2, the coated vehicle 100 can include a first layer 120 of oxidation inhibitor located on the top surface 114 and a second layer 122 of oxidation inhibitor located on the bottom surface 112 of the substrate 110. In still further embodiments, the substrate 110 may be fully coated (e.g., the substrate 110 may have layers of oxidative inhibitor 120/122/124/126 on both the top and bottom surfaces 112/114 and on each of the side surfaces/edges 116A-D). It should be noted that the oxidation inhibitor may be applied to the substrate 110 in several ways. For example, the EUK-207, Monosodium Luminol, or phenyl N-t-butylnitrone may be applied to the substrate using solvent-based coating processes, direct deposition coating processes, or other coating processes known in the art.

Figure 4A:
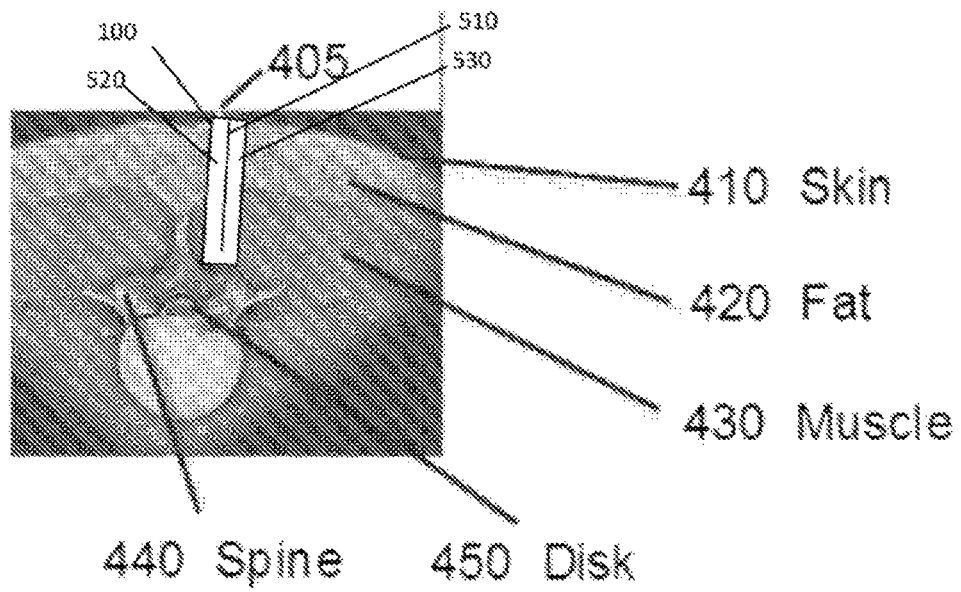
FIGS. 4A-4C show an incision site with the coated films of FIGS. 1-3 inserted in accordance with some of the embodiments of the present technology.

As noted above, various embodiments of the present technology may be used to reduce scarring and inflammation at surgical sites (e.g., incisions). As shown in FIG. 4A, one such incision/surgical site 405 may be the site of spinal surgery. During spinal surgery, the physician must cut through numerous layers of the patient's tissue to gain access to the spine 440 (including disks 450). For example, the physician must cut through the skin 410, fat 420, and muscle 430.

Figure 4B:
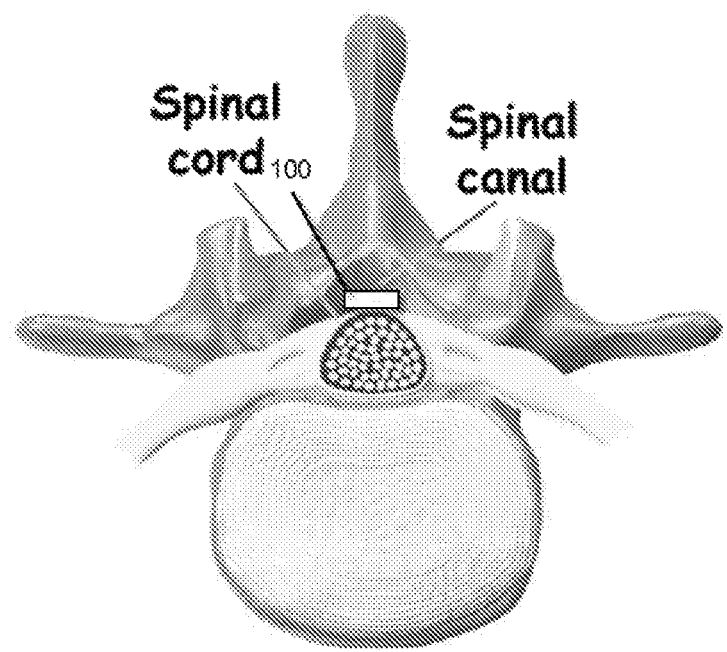
Figure 4C:
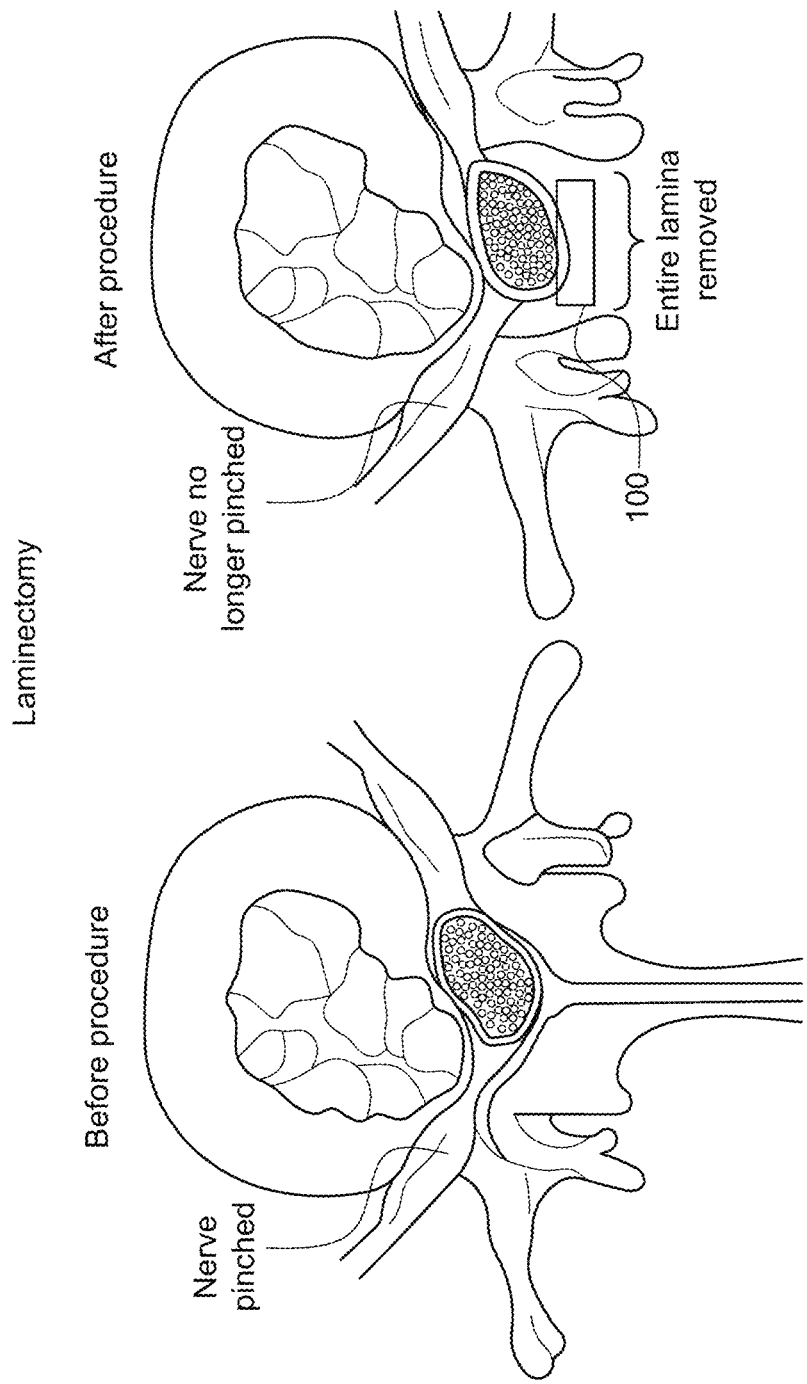

Once the physician has completed his work on the spine 440, to help prevent neuron death, excess inflammation and scarring at the incision site, the physician may introduce the coated vehicle 100 into the site of disease 405 or directly on spine and lumbar or in epidural space or in disc space. To that end, the physician may first cut the vehicle 100/substrate 110 to the appropriate size and shape (e.g., based on the size and shape of the incision, the type of procedure being performed, patient characteristics, etc.). Then, the physician may place the coated substrate 110 into the site of disease 405 such that it rests against the exposed tissue of the patient or lumbar depending on physician's best judgement (FIGS. 4A, 4B, and 4C).

It is important to note that the physician may determine, based on the site of disease, patient and type of vehicle (e.g., if the substrate 110 is coated on the top, bottom, or both the top and bottom), at the time of the procedure or as part of standard pain therapy, the most appropriate manner in which to apply the coated vehicle 100. For example, the physician may apply the coated vehicle 100 directly on the epidural space during a laminectomy, discectomy, laminotomy, or fusion, and between abdominal tissue layers during gastrointestinal surgery. Furthermore, the physician may slightly fold the substrate 110 and place the vehicle 100 into the site of disease such that the one portion of the vehicle 100 (e.g., the portion 520 on one side of the fold 510) rests against the tissue on one side of the incision and another portion of the vehicle 100 (e.g., the portion 530 on the other side of the fold 510) rests against the tissue on the other side of the incision. Alternatively, the physician may only apply the coated vehicle 100 to one side of the incision or may cut two separate pieces and apply one piece to one side of the incision and the other to the other side of the incision. Alternatively, the physician may apply the substrate as part of an injection targeted at the site of disease housed in a syringe or catheter or pump wherein the substrate can be in gel, foam or liquid form. Alternatively, the physician may apply the substrate as part of a minimally invasive procedure wherein the substrate is housed in a robotic appliance.

In addition to determining the most appropriate way to apply the coated vehicle 100 to the incision site/tissue (e.g., folding the substrate, using one piece, using two pieces, etc.), the physician may also determine at the time of surgery the best orientation of the film within the site of disease. For example, if the coated vehicle 100 has only a single layer 120 of oxidation inhibitor on either the top 114 or bottom 112 surface of the substrate, the physician may determine whether it is best to apply the coated vehicle 100 with the coated side facing and contacting the tissue or facing away from the tissue.

Figure 5:
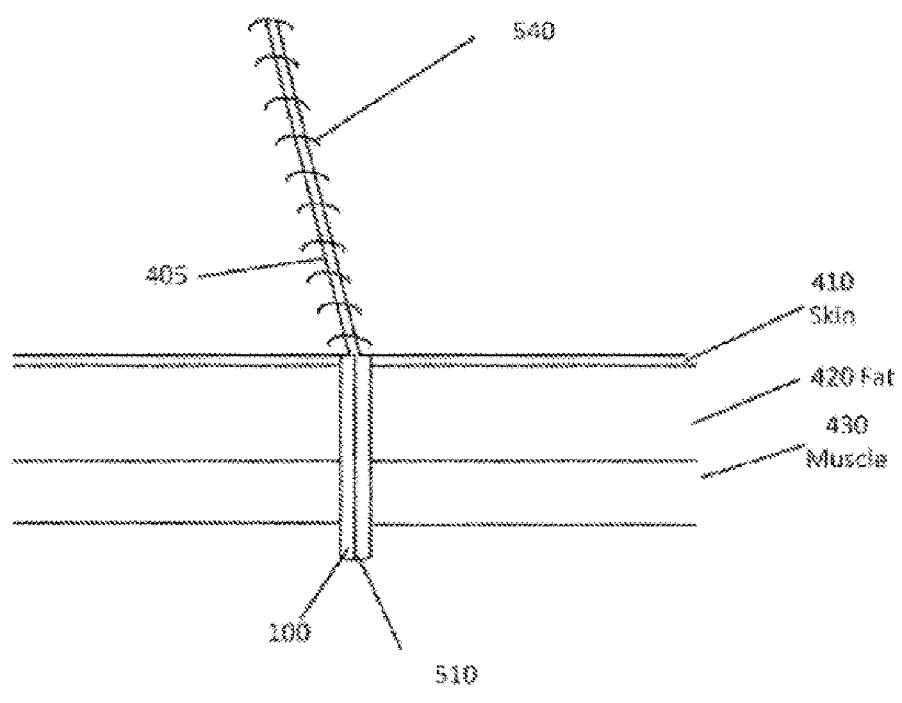
FIG. 5 schematically shows the incision site of FIG. 4A demonstrating the application of the substrate as part of a surgery with the coated film inserted at the site of the disease in accordance with some embodiments of the present technology.
Figure 6A:
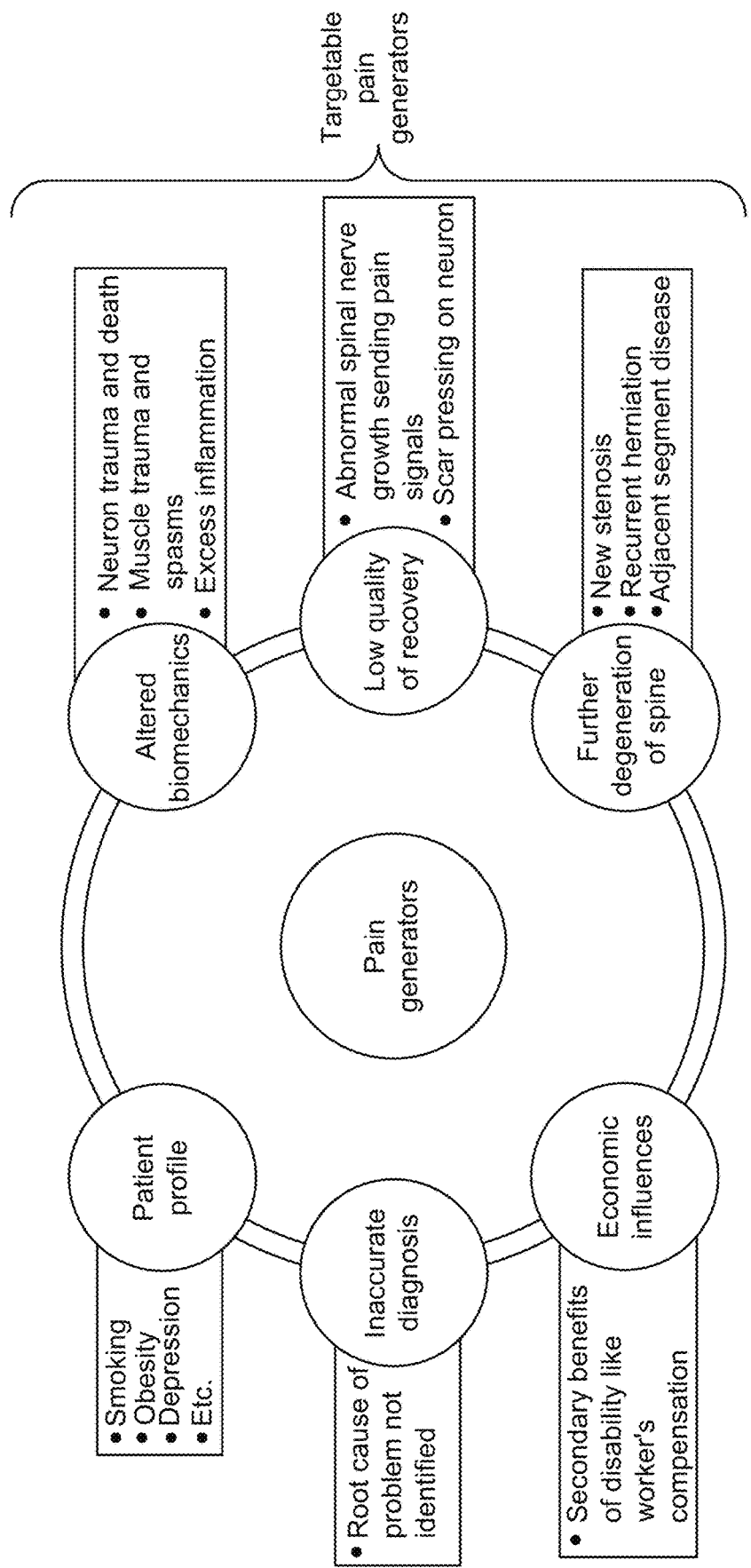
FIG. 6A is a schematic diagram showing examples of pain generators in post-laminectomy syndrome that can be targeted using the methods and devices of the present technology.
Figure 6B:
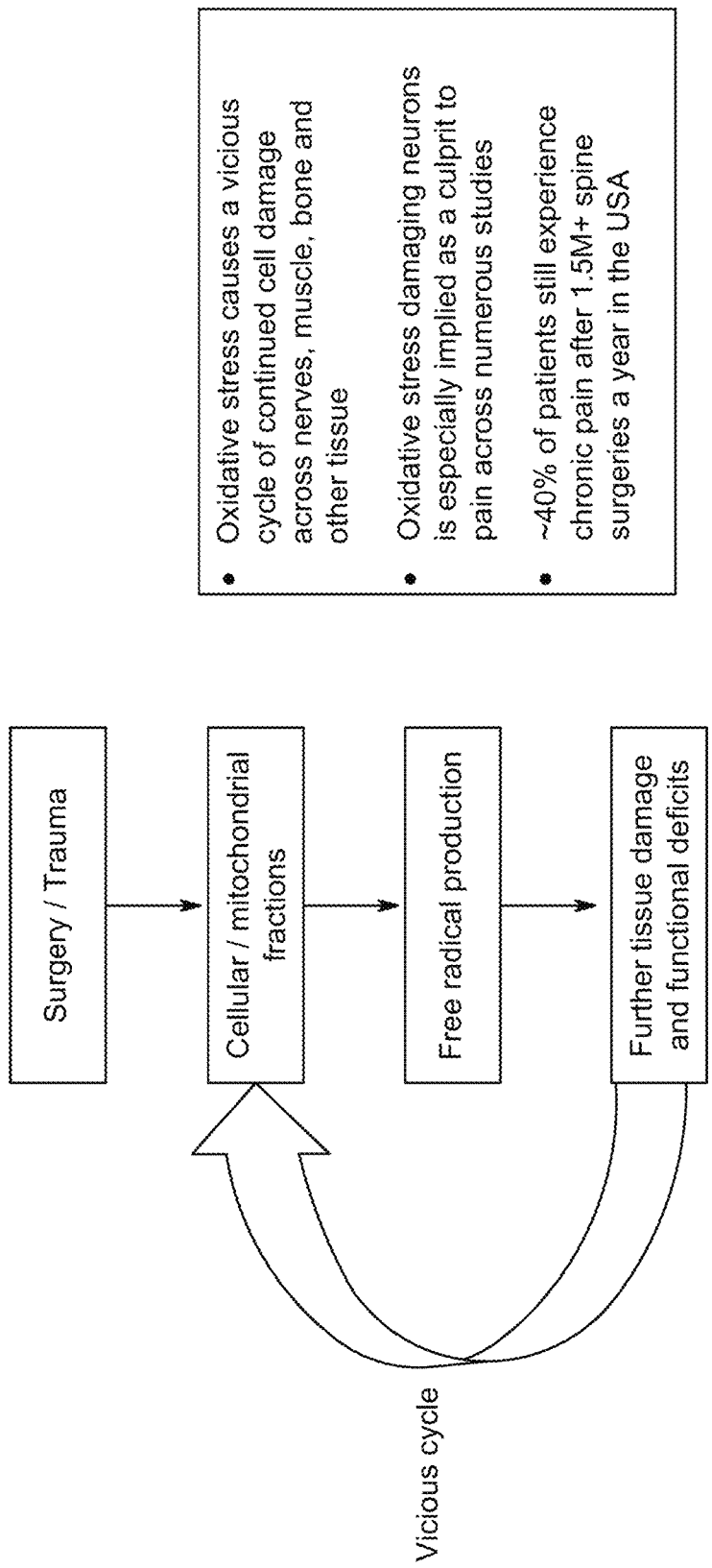
FIG. 6B depicts how oxidative stress is involved in post-laminectomy syndrome.
Figure 7:
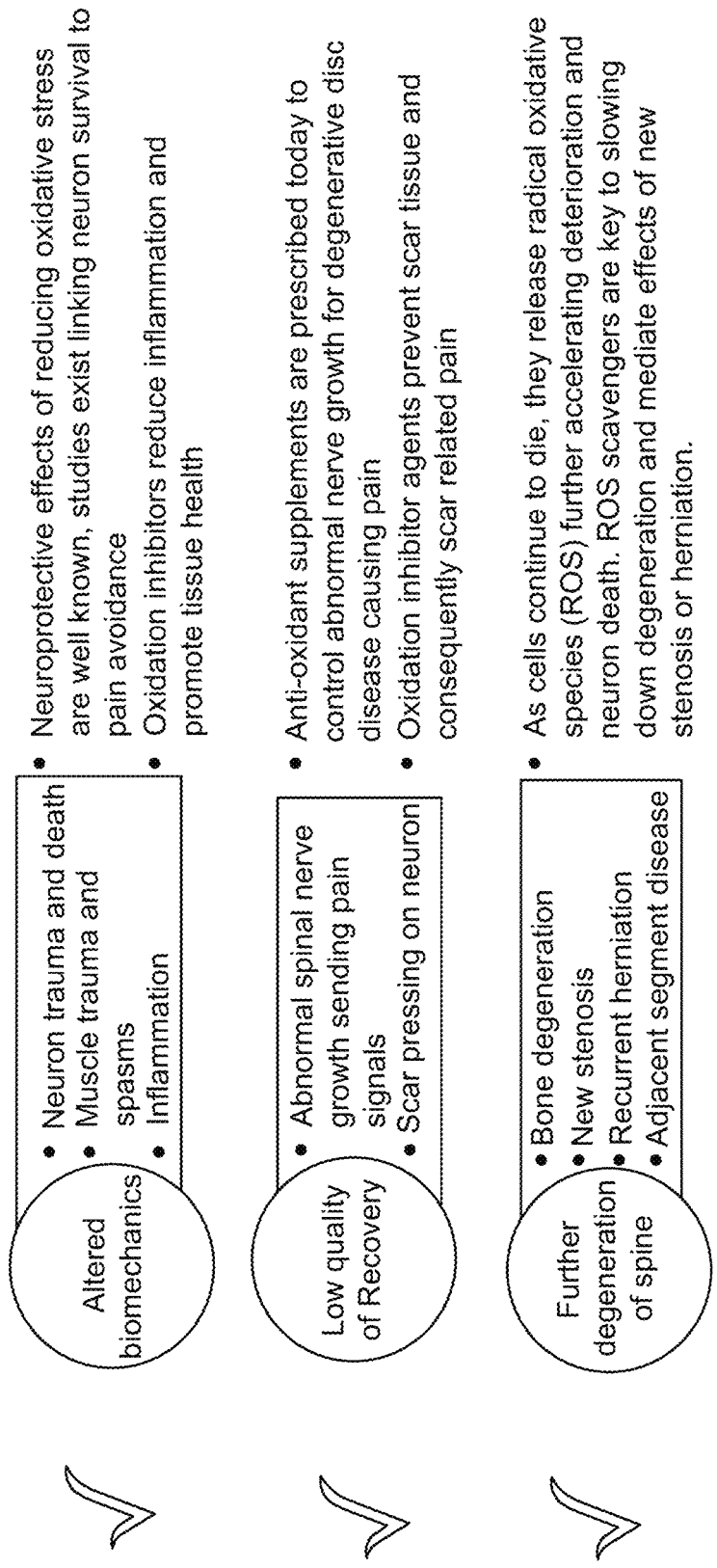
FIG. 7 is a schematic diagram listing examples of conditions in which reducing oxidative stress will neutralize relevant pain generators.
Figure 8:
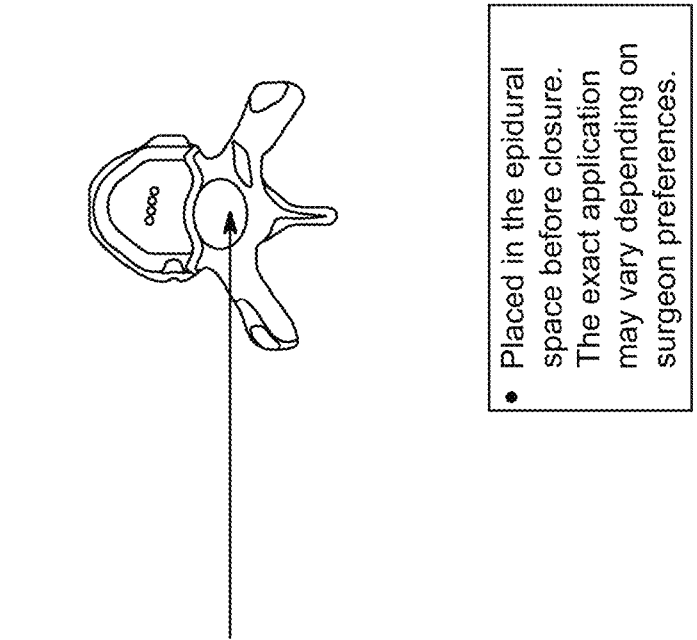
FIG. 8 is a schematic diagram showing dispensing of oxidation inhibitor through a polymer-based film in the spinal canal.
Figure 8:
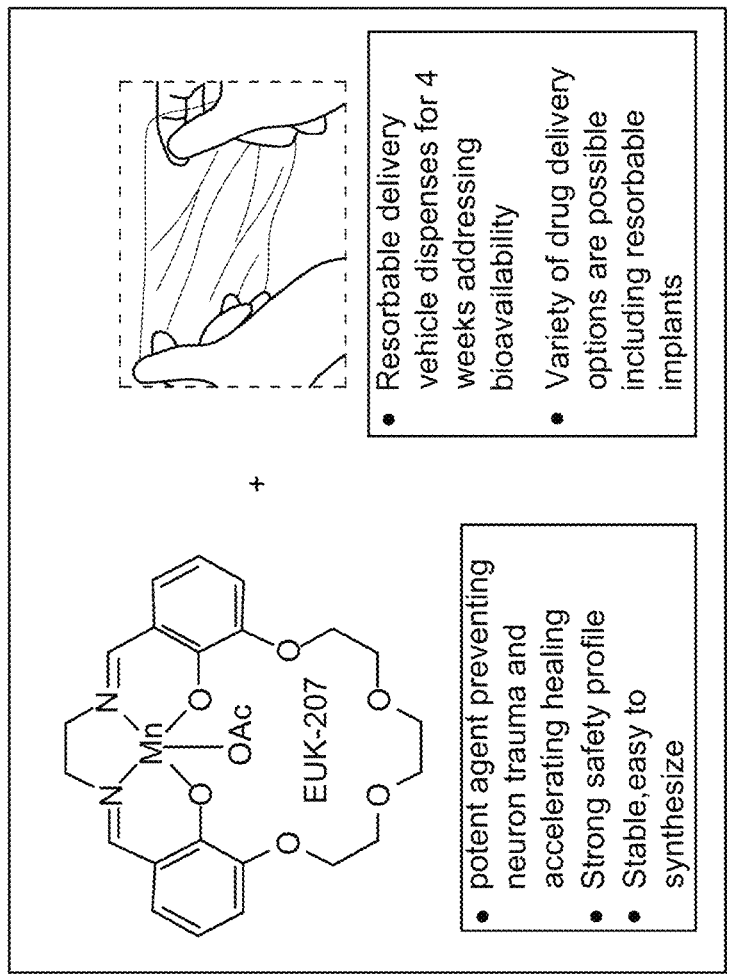
Figure 9:
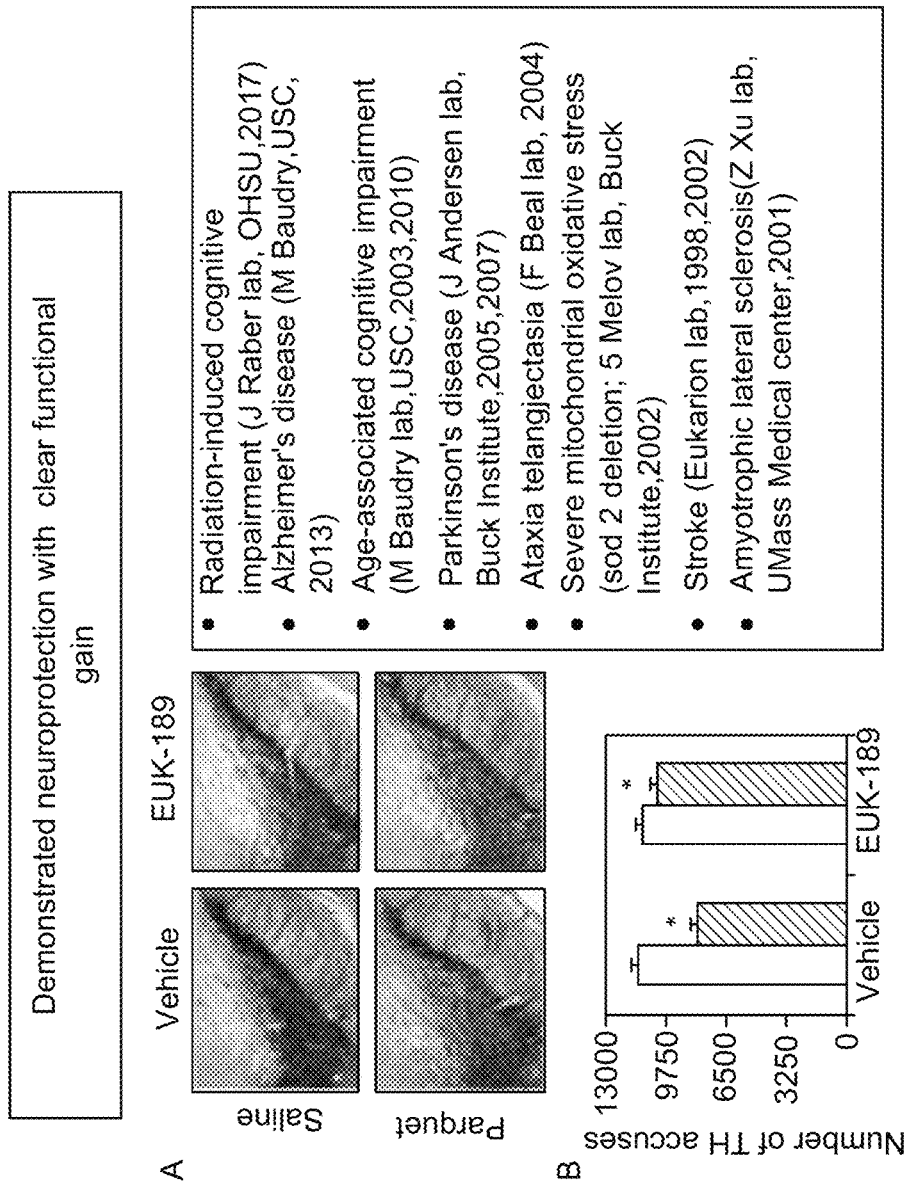
FIG. 9 shows results from prior art for the effectiveness of EUK-189 and EUK 207 in neuroprotection and tissue healing, respectively.
Figure 9:
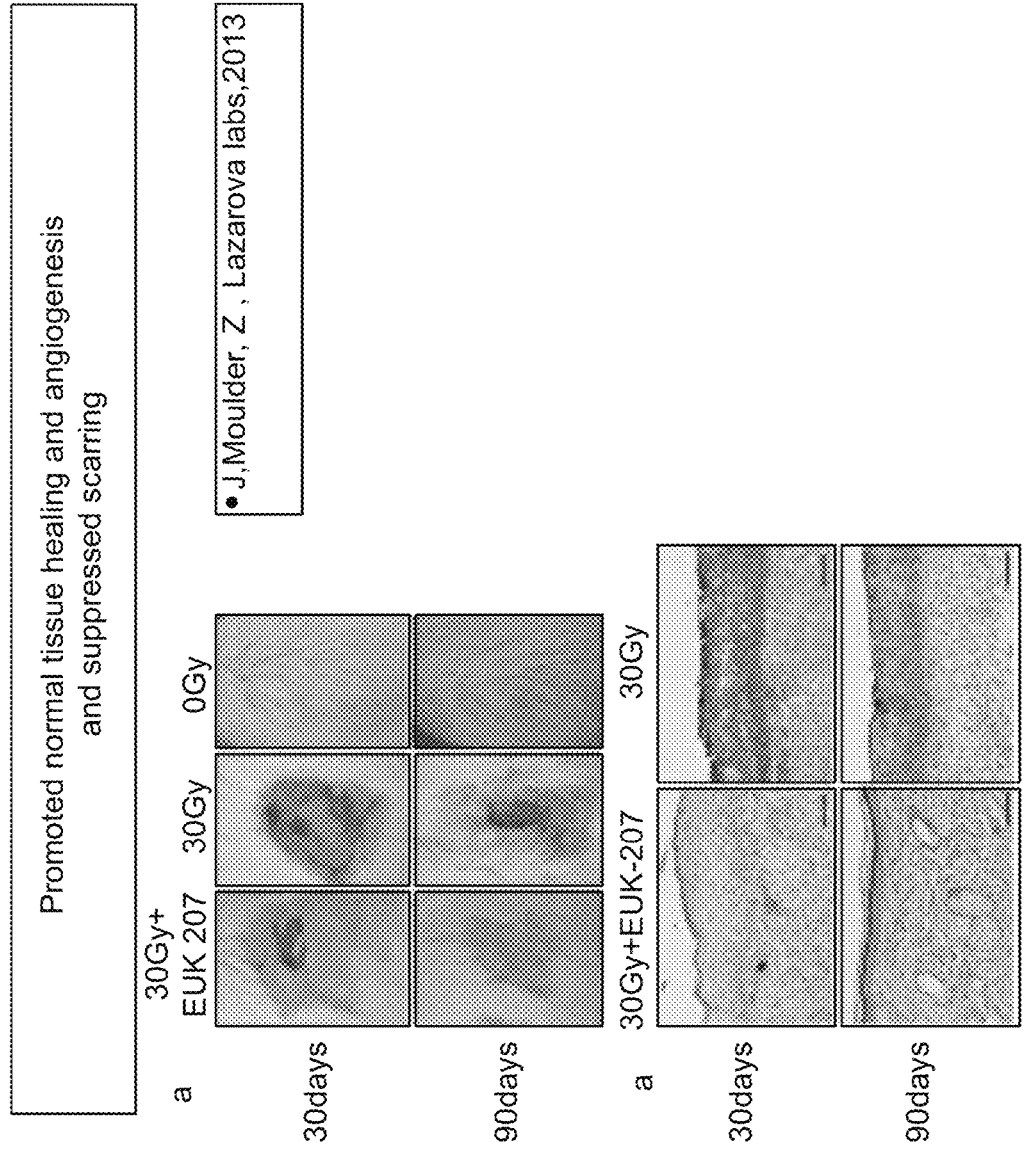

Once the coated vehicle 100 is in place within the site of disease, the physician may close and suture the incision (e.g., using sutures 540; FIG. 5) if applied as part of a surgery. At this point, the coated vehicle 100 is trapped/enclosed within the closed incision 405 and is located between the two sides of the tissue that was cut during the incision (e.g., between the two sides of the skin, fat, muscle, etc.). As with FIGS. 4A-4C, it should be noted that the vehicle 100/substrate 110 is applied on the dura matter, in the spinal canal itself. As noted above, the substrate 110 may be bioabsorbable. Therefore, when the incision 405 is closed, the substrate 110 will begin to break down and will allow the layer(s) of oxidation inhibitor to contact the tissue at the site of disease. The oxidation inhibitor will then begin to trigger the patient's natural anti-oxidant and anti-inflammatory defenses to accelerate recovery and prevent neuron death, excessive inflammation, and formation of fibroblasts.

The coated vehicle 100 provides numerous additional benefits to the patient. For example, because the oxidation inhibitor prevents neuron death, excess inflammation, and formation of excessive fibroblasts, the present technology also reduces pain either as part of standard pain therapy or post procedure and potentially prevents paralysis, increases mobility, decreases post-op complications, and accelerates recovery.

It should be noted that the example given above (e.g., a spinal surgery) is just one example of surgery/procedure in which embodiments of the present technology may be used. Various embodiments of the present technology may be used for any number of surgeries/procedures including, for example, gastro-intestinal surgeries, knee surgeries, hip surgeries, caesarean sections, shoulder surgeries, to name but a few. Additionally, embodiments of the present technology may similarly be used for injuries. For example, if a patient/subject suffers a significant cut/laceration, the physician may insert the coated vehicle 100 into the cut/laceration prior to stitching up the injury.

It is also important to note that, although vehicle 100 is discussed above as being a coated film, other embodiments of the present technology may utilize different structures and/or substrates. For example, the vehicle/substrate may be a syringe, a catheter, a pump, a mesh, a scaffold, a gel or suture, for example, depending on the exact nature of the procedure or therapy. Additionally, in some embodiments, the oxidative inhibitor may be infused into the material of the vehicle/substrate (e.g., in addition to or instead of the oxidation inhibitor layer(s) discussed above), particularly in gel embodiments used in syringes.

Furthermore, one or more embodiments of the present technology may be used in conjunction with one another to further protect neurons and reduce scarring and inflammation. For example, in the spinal surgery example provided above, the sutures 540 used to close the incision 405 may be coated and/or infused with an oxidation inhibitor. Additionally, or alternatively, an oxidation inhibitor infused gel may be applied to the site of disease before and/or after closing the incision. In such cases, various embodiments of the present technology may help to protect tissue (e.g., the substrate 110/vehicle 100 may protect tissue between the fat 420, muscle 430, etc.) and reduce the external scarring (e.g., the sutures 540 and/or gel may reduce the scarring at the skin 410)

EXAMPLES

Example 1. Prevention of Neuron Death by Administering Anti-Oxidant Agents

Inhibition of neuron death using one of the anti-oxidant agents described above is examined in a spinal injury model as described below. The oxidation inhibitor used is phenyl-N-tert-butylnitrone, a ROS scavenger. Peripheral nerve injury is induced by tightly ligating the L5 spinal nerve under isoflurane anesthesia (2% induction and 1.5% maintenance). Seven days after SNL, mice are randomly divided into treatment and control groups. Mice belonging to one treatment group are injected by one of two different routes with phenyl-N-tert-butylnitrone, PBN (Sigma, St. Louis, Mo.). Doses of PBN used are 150 mg/kg (i.p., 0.1 ml) or 100 μg (i.t., 5 μl), dissolved in saline at a concentration of 20 mg/ml. Mice in the control groups are treated with the same volume of saline. Non-ligated mice are divided into four groups, three injected intrathecally with 0.05, 0.10, or 0.25 μg of an ROS donor, an organic hydroperoxide, and tert-butyl hydroperoxide (t-BOOH) (Sigma) dissolved in 5 μl saline and the remaining group being injected intrathecally with 5 μl saline alone to serve as control.

Effect of administering PBN on Gabaergic neurons is also tested using the GABAA receptor antagonist bicuculline (1(S), 9(R)-(−)-Bicuculline methiodide), the GABAA receptor antagonist. Seven days after SNL, mice are randomly divided into two treatment groups and one control group. The treatment group mice receive one of two doses (0.05 μg or 0.10 μg dissolved in 5 μl saline) of bicuculline (Sigma) intrathecally. The control group mice receive 5 μl saline intrathecally. Immediately after the intrathecal injection, all groups receive an intraperitoneal injection of 150 mg/kg PBN dissolved in 0.1 ml saline.

Pain behavior is tested by assessing mechanical hyperalgesia of the affected hind paw. All experiments are conducted by a person blind with respect to the different groups. Mechanical hyperalgesia of the hind paw is measured by determining the frequency of foot withdrawals to 10 stimuli applied with a von Frey (vF) filament (Stoelting, Wood Dale, Ill.). Mice are placed in a plastic box (4×4×12 cm) on a metal grid floor and acclimated to the box for 8-10 minutes prior to testing. The vF filament is applied from underneath the skin on the left hind-paw between the 3rd and 4th digits. The hind-paw is stimulated with the filament vF #3.0, which is equivalent to 0.1 grams of bending force. The vF filament is applied perpendicularly for 2-3 seconds with enough force to bend it slightly. A positive response consists of an abrupt withdrawal of the foot during or immediately after stimulation. Response rates are calculated as a percentage of the number of positive responses/10 stimuli.

PBN treated mice are expected to withdraw their foot less abruptly reflecting reduced experience of pain, which would be consistent with reduction of oxidative stress and the resulting protection of GABA neurons. Oxidative stress kills GABA neurons and protection of GABA neurons is known to reduce sensation of pain. Conversely, mice treated with bicuculline in addition to PBN are expected to withdraw their foot relatively fast reflecting increased experience of pain, given that bicuculline is a competitive antagonist of GABAA transmission in the spinal cord.

For cellular studies, lumbar spinal cord of the experimental mouse is removed under anesthesia (1.5 g/kg, urethane administered i.p.) and placed in pre-oxygenated, cold (<4° C.) artificial cerebrospinal fluid (ACSF) (composition in mM: NaCl, 117; KCl, 3.6; CaCl2, 2.5; MgCl2, 1.2; NaH2PO4, 1.2; NaHCO3, 25; glucose 11), saturated with 95% $O_2$ and 5% $CO_2$ mixed gas. The spinal cord is trimmed and embedded in a 3% agar block and sliced transversely at a thickness of 350 μm using a vibratome (Leica, VT1000S) in order to perform electrophysiological recordings. The spinal cord slices are incubated for 1 hour in ACSF at 33° C. An individual slice is placed in a recording chamber and fixed with a grid of parallel nylon threads supported by a U-shaped stainless-steel weight. The ACSF saturated with 95% $O_2$-5% $CO_2$ is perfused into the chamber at 2 ml/min. Signals are recorded with a Multiclamp 700B amplifier (Axon Instruments; Union City, Calif.), digitized at 10 kHz with a DigiDATA (Axon Instruments; Union City, Calif.), and filtered at 1-2 kHz. The data files are saved in a PC-based computer using the pCLAMP9 acquisition software (Molecular Devices; Union City, Calif.).

For whole-cell recordings, conventional whole-cell patch recording is made at room temperature, with patch pipettes (4-6 MΩ) filled with a potassium gluconate internal solution (composition in mM: K-gluconate, 120; KCl, 10; Mg-ATP, 2; Na-GTP, 0.5; EGTA, 0.5; HEPES, 20; phosphocreatine, 10). The position of neurons in lamina II is identified using differential-interference contrast optics (DIC) at 40× magnification. In every voltage clamp recording, an equilibration period of 10 to 15 min is allowed after whole cell access is established and the recording reaches a steady state. The recording is discarded if the monitored input resistance changed >15%. Miniature excitatory post-synaptic currents (mEPSCs) are recorded in the presence of 1 µM TTX and 10 µM bicuculline at a holding potential of −70 mV. Miniature inhibitory post-synaptic currents (mIPSCs) are recorded in the presence of 1 µM TTX, 20 µM CNQX, and 50 µM D-AP5 (D-2-amino-5-phosphonopentanoic acid, Sigma) at a holding potential of 0 mV. The mIPSCs are isolated into GABAA-receptor mediated and glycine-receptor mediated mIPSCs by 0.5 µM strychnine and 10 µM bicuculline, respectively, at a holding potential of 0 mV.

PBN treated mice are expected to demonstrate superior action potential discharge (excitatory) pattern for surviving neurons since oxidative stress not only kills GABA neurons but also suppresses firing activity of surviving GABA neurons. As discussed above, suppression of GABA transmission leads to pain. PBN treatment is expected to restore excitability and prevent suppression of firing activity. Bicuculline is expected to counter the effect of PBN.

Next, varying amounts of PBN are applied as a layer on different samples of bioabsorbable substrates (FIG. 1) for implanting into the incision sites of laminectomized rats. These PBN amounts are chosen based on the positive results (less abrupt foot withdrawal and/or superior excitatory action potential discharge) resulting from PBN injection. The PBN containing substrates are inserted into the incision sites of laminectomized rats. Control laminectomized rats are implanted with bioabsorbable substrate not containing PBN. The incisions are closed, and the pain behavior is measured several times during the first four to five weeks.

The procedure described above is repeated using EUK-207 or monosodium luminol as the oxidation inhibitor.

Example 2. Inhibition of Adhesion Formation by the Oxidation Inhibitors

The method to achieve inhibition of neuron death and excess inflammation and adhesion formation by administering an oxidative inhibitor post-laminectomy is carried out as described in the following. The oxidation inhibitor used is EUK-207. Laminectomy is performed on rats and the ability of the administered EUK-207 to reduce scar tissue formation in the epidural space is examined. Towards this, histological analysis is used to determine the differences in epidural fibrosis (EF) thickness between the treated and control groups of rats.

A total of 36 young adult Sprague Dawley male rats (Charles River Lab; 350-375 g) are randomly assigned to three experimental groups (n=12/group): Group A Control-Vehicle only, Group B Experimental—Hi Dose EUK-207, Group C Experimental—Lo Dose EUK-207. The rats are anesthetized by intraperitoneal injection of ketamine (35 mg/kg) and xylazine (10 mg/kg). Adequate depth of anesthesia is assessed by lack of withdrawal to hindlimb pinch and loss of eyeblink reflex. Once anesthetized, animals receive cefazolin sodium for infection prevention (~40 mg/kg, i.p.) and buprenorphine (~0.1 mg/kg, s.c.) for minimizing pain and discomfort. Sodium Chloride ophthalmic ointment (e.g. Muro 128 Sterile Ophthalmic 5% Ointment) is applied to the eyes before surgery. All animals undergo laminectomy.

The lower back of each rat is shaved, and the surgical area is sterilized using povidone iodine. A midline skin incision from L-2 to L-5 is performed. The lumbosacral fascia is incised and the paraspinous muscles dissected to expose the L3-5 laminae. A total L-3-5 Laminectomy is carried out and ligamentum flavum and epidural fat are removed. Hemostasis is managed using surgical sponges when necessary. Care is taken to avoid injury to the dura.

At the time of laminectomy, a subcutaneous pocket for placing a pump (Alzet implantable pump #2006) is created next to the laminectomy site by dissection. APE 10 tube is attached to the pump and the tip of the tube is sutured to the paraspinous muscles such that EUK-207 is delivered directly to the exposed dura covering the spinal cord at the rate of 0.15 µl/hr for 28 days. The underlying fascia is closed in layers with suture and the skin closed with surgical staples. The Alzet pump serves the same purpose as the substrate (bioabsorbable film) would, i.e., allows EUK-207 to be delivered precisely on the epidural surface in the spinal canal. The film is placed in the spinal canal.

On day 28, the rats are sacrificed and the lumbar dura extending between L3 to L5 level are removed en bloc and placed in 10% buffered formalin. After decalcification and dehydration, paraffin blocks are prepared. Next, axial 8-µm-thick sections of dura are cut and stained with toluidine blue and mounted on slides for analysis.

Slide specimens are analyzed using Image Pro Plus (Media Cybernetics software) to measure the density of epidural fibrosis. The following formula is used to measure the adhesion profile.

Epidural fibrosis thickness (m)=Epidural fibrosis thickness+Dural thickness. Statistical Analysis of Variance (ANOVA) is used to test differences in thickness between the means of all groups Inhibition of adhesion formation is achieved if the measured EF thickness is of a lower magnitude in the treated rats as compared to the control rats. Next, varying amounts of EUK-207 are applied as a layer on different samples of bioabsorbable substrates for implanting into the incision sites of laminectomized rats. These EUK-207 amounts are chosen based on the positive results (lower EF thickness in treated mice) of the pump-delivered EUK-207 described above. The EUK-207 containing substrates are inserted into the incision sites of laminectomized rats. Control laminectomized rats are implanted with bioabsorbable substrate not containing EUK-207. The incisions are closed and the EF thickness in each mouse is measured after 28 days.

The procedure described above is repeated using monosodium luminol or phenyl N-t-butylnitrone as the oxidation inhibitor.

Example 3. Slowing Disc Degeneration by Administering Extended Release Anti-Oxidant Agent Via Gel in the Disc Space Oxidative stress plays a role in the complex pathology of degenerative disc disease. Treatment with an anti-oxidant may slow the progression of disc degeneration. Slowing degeneration of the disc using one of the anti-oxidant agents described above is examined in a disc injury model. The model involves percutaneous needle puncture in rats which induces degenerative signs in discs similar to those of human discs. The short duration of action of anti-oxidant small molecules is prolonged by using a controlled release poloxamer gel formulation which can house the drug agent up to 4 weeks. Twenty four Wistar rats are used. EUK 207, a ROS scavenger is used as the oxidation inhibitor. Preoperative radiograph and MM scans are conducted as a baseline measurement of selected disc heights for all rats. Rats are anesthetized. Disc injury is induced by needle puncture at coccygeal intervertebral levels Co6-7 and Co8-9. Tail puncture model permits simple, efficient and inexpensive way of modeling disc degeneration without the need for surgery. A 20-gauge needle is inserted at the level of the annulus fibrosus of Co6-7 (proximal) and Co8-9 (distal), crossing the nucleus pulposus up to the contralateral annulus fibrosus. After full penetration, the needle is rotated 360° twice and held for 30 seconds to induce damage to the disc material. Simultaneously, the poloxamer gel containing 100 µg/mL of EUK 207 is injected into the selected discs of 12 rats in the intervention group, and saline is injected into the selected disks of the 12 rats in the control group. EUK 207 gel and saline injections into the disc space are repeated every four weeks. Reduction of disc height is measured in the intervention vs control groups by radiograph and MRI scans after 4 and 12 weeks.

After 12 weeks, rats are sacrificed and histological assessment is conducted. Histological and image measurements include disc space narrowing, decreased disc height, water content reduction, and histological disorganization.

Anti-oxidant drug provided via a gel formulation in the disc space is expected to (i) decrease or prevent the narrowing of the disc space, (ii) reduce or prevent the decrease in disc height, and (iii) lead to the discs having higher water content relative to the control group. The inflammation, as assessed by histological and image assessments, is also expected to be reduced.

Example 4. Reducing Inflammation and Scarring in Stenosis by Persistent Anti-Oxidant Agents in the Epidural Space Anti-oxidant molecules may reduce inflammation and scarring. Reducing pain generating inflammatory chemicals that result from stenosis using one of the anti-oxidant agents described above is examined in a spine injury model as described below. Chronic compression of the dorsal root ganglion method is used to mimic the effects of stenosis in rats. 24 young male Sprague Dawley rats, each weighing 200-250 g, are used. EUK 207, a ROS scavenger, is used as the oxidation inhibitor. Rats are anesthetized. L4/L5 invertebral foramina are exposed via incision. Stainless steel rods are implanted unilaterally, one rod for each vertebra to chronically compress the lumbar dorsal root ganglion. An L-shaped needle is inserted into the intervertebral foramen at 30° with respect to the dorsal midline and 10° with respect to the vertebral horizontal line. The needle is withdrawn upon a twitch from the hind leg. Then, a fine, L-shaped stainless-steel rod, 4 mm in length and 0.5 mm in diameter, is inserted along the path of the needle.

The intraforaminal implantation of the rods results in inflammatory reactions and disruptions in the excitatory action of neurons causing spontaneous action potentials which are in turn experienced as pain by the animals, mimicking the pain caused by stenosis in humans.

Post implantation surgery, an epidural catheterization is performed at T13-L1 intervertebral space. A polyethylene tube is inserted into the epidural space and gently advanced ~3.0 cm in a caudal direction to place its tip between the L4 and L5 levels. All animals are allowed to recover for 3 days after epidural catheterization.

12 rats in the intervention group receive 10 µg/mL of EUK 207 daily via injection in the epidural space. In the control group, 12 rats receive saline for 4 weeks in the epidural space.

Behavioral testing is performed every day during daytime to measure mechanical threshold and motor function which are assessed on a four-level scale. 1=normal gait with no foot deformities; grade 2=normal gait with a marked foot deformity; grade 3=slight gait disturbance in which a foot drop was present; and grade 4=severe gait disturbance with motor paresis. The rats are monitored for behavioral changes including posture, lameness, and change in eating habits.

Rats are sacrificed after 4 weeks. Adhesion and inflammation around the neural foramen are assessed via histological analysis.

Relative to untreated animals, repeated anti-oxidant treatment in the epidural space in a disease of the spine is expected to result in reduced inflammation and scarring leading to reduction in pain and increased motor function and.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present technology, and without departing from the spirit and scope thereof, can make various changes and modifications of the technology to adapt it to various usages and conditions. Thus, other embodiments are also within the scope of the following claims.

What is claimed is:

1. A method for treating pain associated with a disease of the spine in a subject in need thereof, the method comprising:
    injecting a pharmaceutical composition into a spinal space of the subject, the pharmaceutical composition comprising a bioabsorbable substrate and an oxidation inhibitor;
    wherein the substrate is capable of being absorbed when injected into the spinal space and is a prolonged release delivery vehicle,
    wherein the oxidation inhibitor is capable of triggering the subject's anti-oxidant defenses, whereby the pain is reduced or eliminated, and
    wherein the only oxidation inhibitor administered in said method is a small molecule mimetic of superoxide dismutase and catalase, and
    wherein the oxidation inhibitor is EUK-8, EUK-189 or EUK-207.

2. The method of claim 1, wherein the spinal space is one or more spaces selected from the group consisting of: epidural space, disc space, subarachnoid space, nucleus pulposus, and intervertebral space.

3. The method of claim 1, wherein the oxidation inhibitor is EUK-8.

4. The method of claim 1, wherein the oxidation inhibitor is EUK-189.

5. The method of claim 1, wherein the oxidation inhibitor is EUK-207.

6. The method of claim 1, wherein the bioabsorbable substrate is a gel or a foam.

7. The method of claim 1, wherein the disease is selected from the group consisting of degenerative disc disease, spondylolisthesis, spondylolysis, osteomyelitis, stenosis, disc herniation, and scoliosis.

8. The method of claim 1, wherein the oxidation inhibitor is EUK-189, and the disease is degenerative disc disease.

9. The method of claim 1, wherein the bioabsorbable substrate releases the oxidation inhibitor over several weeks.

10. The method of claim 1, wherein the bioabsorbable substrate is a controlled release gel.

11. The method of claim 10, wherein the controlled release gel releases the oxidation inhibitor for up to four weeks.

* * * * *